United States Patent [19]

Siegemund et al.

[11] Patent Number: 4,623,491
[45] Date of Patent: Nov. 18, 1986

[54] PROCESS FOR THE PREPARATION OF HALOGENATED ALIPHATIC CARBOXYLIC ACID FLUORIDES

[75] Inventors: Günter Siegemund, Hofheim am Taunus; Werner Schwertfeger, Langgöns, both of Fed. Rep. of Germany

[73] Assignee: Hoechst Aktiengesellschaft, Frankfurt, Fed. Rep. of Germany

[21] Appl. No.: 745,254

[22] Filed: Jun. 14, 1985

[30] Foreign Application Priority Data

Jun. 18, 1984 [DE] Fed. Rep. of Germany ....... 3422576

[51] Int. Cl.$^4$ .............................................. C07C 51/60
[52] U.S. Cl. ................................................. 260/544 F
[58] Field of Search ........... 260/544 F, 544 D, 544 K, 260/544 M

[56] References Cited

U.S. PATENT DOCUMENTS 3,449,416 6/1969 Brotherton ..................... 260/544 M

FOREIGN PATENT DOCUMENTS 0088258 2/1983 European Pat. Off. .

OTHER PUBLICATIONS

Conant, James Bryant et al., *The Chemistry of Organic Compounds*, 4th Ed. (1955) MacMillan, Publ., pp. 300-301 and 410-411.
Houben/Weyl, *Methoden der organischen Chemie* (1952) vol. VIII/3, pp. 472-473.
Henne, Albert L. et al., *J. Am. Chem. Society*, vol. 60 (1938) pp. 1697-1698.
Krauch, Helmut et al., *Organic Name Reactions* (1964) John Wiley & Sons, Publ., pp. 218-219.
C. Ferri, "Reactions of Organic Synthesis", G. Thieme Verlag, Stuttgart, 1978, 460.
Houben-Weyl, *Methoden der organischen Chemie*, vol. V/4, pp. 688-689 (1960).

*Primary Examiner*—Natalie Trousof
*Assistant Examiner*—L. Hendriksen
*Attorney, Agent, or Firm*—Curtis, Morris & Safford

[57] ABSTRACT

Halogenated aliphatic carboxylic acid fluorides are prepared by reacting halogenated aliphatic carboxylic acids with trihalogenomethyl aromatic compounds containing, as a predominant total or exclusively, fluorine atoms in the trihalogenomethyl groups, in particular with benzotrifluoride, in the presence of Lewis acids as catalysts. The reaction products are intermediate products having a multiplicity of uses.

14 Claims, No Drawings

PROCESS FOR THE PREPARATION OF HALOGENATED ALIPHATIC CARBOXYLIC ACID FLUORIDES

Halogenated aliphatic carboxylic acid fluorides are intermediates which have a multiplicity of uses. Thus, for example, ω-H-perfluoropropionyl fluoride can be converted into ω-H-perfluoropropyl-vinyl-ether by the following scheme of reactions:

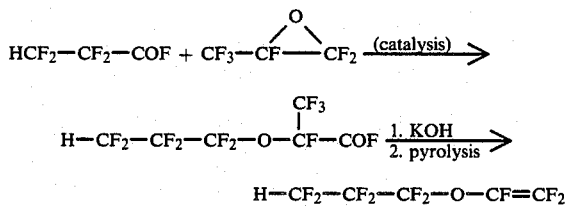

ω-H-Perfluoropropyl-vinyl-ether is an important co-monomer for the preparation of perfluorinated ion exchange resins (cf. No. EP-A-0,088,285). There are various possible means of synthesizing carboxylic acid fluorides, most of which start from the parent carboxylic acids. These processes, can in turn, be subdivided principally into 1-stage and 2-stage processes.

In the one-stage processes, the free carboxylic acids are converted directly, by means of suitable fluorinating agents, into the corresponding carboxylic acid fluorides:

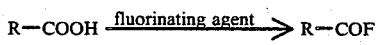

(R = organic radical)

The suitability of various fluorinating agents for this purpose has been investigated in detail, inter alia, in the paper by D. G. Cox et al., J. Fluorine Chemistry 23 (1983), 383–388. Amongst the fluorinating agents tested, sulfur tetrafluoride, $SF_4$, diethylamino-sulfur trifluoride, $(C_2H_5)_2NSF_3$, the Yarovenko reagent, $(C_2H_5)_2N-CF_2-CFClH$, perfluoro-2-methyl-2-pentene,

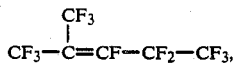

fluorosulfonic acid, $FSO_3H$, and the Ishikawa regent, $(C_2H_5)_2N-CF_2-CFH-CF_3$, and the last-mentioned compound (the Ishikawa reagent) was found to be the most suitable. However, the Ishikawa reagent must first be prepared and purified by distillation. D. G. Cox et al., loc. cit., have indicated the following equation for its preparation (from diethylamine and perfluoropropene):

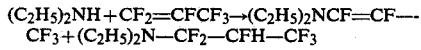

The yield of the mixture of the two reaction products is stated in the experimental part of the abovementioned article to be only 65%.

In the most customary two-stage processes for the preparation of carboxylic acid fluorides from the parent free carboxylic acids, the carboxylic acids are first converted into the carboxylic acid chlorides in the first stage of the reaction:

Chlorinating agents suitable in this case are—for instance according to C. Ferri, Reaktionen der organischen Synthese ("Reactions of Organic Synthesis"), G. Thieme Verlag, Stuttgart 1978, 460, and also Houben-Weyl, Methoden der organischen Chemie ("Methods of Organic Chemistry"), volume VIII/3, 472 (1952)—inter alia, $SO_2+Cl_2$, $SOCl_2$, $PCl_5$, $COCl_2$ and benzotrichloride, $C_6H_5CCl_3$.

For example, chloroacetyl chloride (and benzoyl chloride) are formed in this reaction from monochloroacetic acid and benzotrichloride in the absence of a catalyst at 100° to 120° C. or, in the presence of $ZnCl_2$, at a somewhat lower temperature (80° to 90° C.); the fundamental equation for the reaction is:

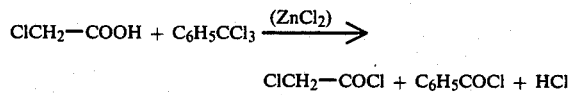

In the second stage of the reaction, the carboxylic acid chlorides are then reacted with fluorinating agents, such as, for example, HF, KF, $KHF_2$, $KSO_2F$, NaF etc.—cf., for example, Houben-Weyl, Methoden der organischen Chemie ("Methods of Organic Chemistry"), volume V/3 (1962), pages 119/120, 148–150 and 171–173:

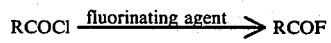

In particular, the necessity for two reaction stages is a disadvantage in the two-stage processes.

If the benzotrichloride is replaced in the abovementioned reaction between carboxylic acids and benzotrichloride by benzotrifluoride no reaction takes place—as our own experiments have shown—at any rate using ω-H-perfluoropropionic acid as the starting carboxylic acid, after heating for several hours at temperatures up to 190° C. in the absence of catalysts.

Nor—also according to our own experiments—does, for instance propionic acid, $C_2H_5-COOH$, react with benzotrifluoride in the presence of catalysts ($TiO_2$/$TiCl_4$) when heated at 130° C. for several hours.

Because of the increased requirement for halogenated aliphatic carboxylic acid fluorides and because the relevant processes of the state of the art are not satisfactory or not wholly satisfactory, it was required to find an improved process for the preparation of halogenated aliphatic carboxylic acid fluorides of this particular type.

It has been possible to achieve this object in accordance with the invention by reacting halogenated aliphatic carboxylic acids with trihalogenomethyl aromatic compounds containing, as a predominant total or exclusively, F atoms in the trihalogenomethyl groups, in the presence of Lewis acids as catalysts. The invention relates, therefore, to a process for the preparation of halogenated aliphatic carboxylic acid fluorides by reacting halogenated aliphatic carboxylic acids with fluorinating reagents; the process comprises using as fluorinating reagents trihalogenomethyl aromatic compounds containing, as a predominant total or exclusively, fluorine atoms in the trihalogenomethyl groups, and carrying out the reaction in the presence of Lewis acids as catalysts.

In accordance with the process, the corresponding halogenated aliphatic carboxylic acid fluorides are obtained in yields of, in some cases, up to about 95% of theory in a one-stage reaction, which is simple to carry out, from halogenated aliphatic carboxylic acids, using fluorinating reagents (benzotrifluoride) and catalysts which are readily accessible on an industrial scale and are cheap. The success of this reaction was extremely surprising, because ω-H-perfluoropropionic acid does not react with benzotrifluoride when heated for several hours at elevated temperatures in the absence of catalysts. It was in no way to be expected that the reaction would only take place as a result of the presence of Lewis acids as catalysts and would then give the corresponding acid fluoride without difficulty, especially since, for instance, the known reaction between monochloroacetic acid and benzotrichloride (cf. Houben-Weyl, volume VIII/3, loc. cit.) takes place in virtually the same manner—merely at slightly different temperatures—either in the absence or in the presence of a catalyst.

Furthermore, the success of the reaction according to the invention was also surprising because propionic acid—not halogenated, however—does not afford any propionyl fluoride either when heated at 130° C. for several hours, even in the presence of Lewis acid catalysts ($TiO_2/TiCl_4$).

Halogenated aliphatic carboxylic acids which can be employed for the process according to the invention are, in principle, all the possible halogenated, unbranched or branched, saturated or unsaturated, monobasic or polybasic, aliphatic carboxylic acids. However, it is preferable to employ halogenated aliphatic carboxylic acids of the formula I:

X—R—COOH   (I)

in which R is a divalent aliphatic $C_1$-$C_{10}$ radical in which at least half of the H atoms have been replaced by halogen—preferably F and/or Cl—and X is H, halogen—preferably F or Cl—or COOH.

The following are examples of halogenated aliphatic carboxylic acids—both those which are preferred and those which are not preferred:
$CCl_3COOH$
$CF_2HCOOH$
$CHFClCOOH$
$CF_3$—COOH
$HCF_2CF_2COOH$
$H(CF_2)_4COOH$
$F_3CCF_2COOH$
$F_3(CF_2)_5COOH$
$F_3C(CF_2)_6COOH$
HOOC—$(CF_2)_2$—COOH
$CF_2BrCOOH$
$F_3C$—$(CF_2)_{12}$—COOH
etc.

The trihalogenomethyl aromatic compounds employed, containing, as a predominant total or exclusively, fluorine atoms in the trihalogenomethyl groups are preferably compounds of the formula II—on their own or as mixtures with one another:

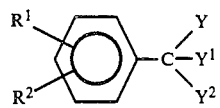

in which Y, $Y^1$ and $Y^2$, independently of one another, are F or Cl and $R^1$ and $R^2$, also independently of one another, are H, halogen—preferably F or Cl—or

it being necessary for at least twice as many F atoms as Cl atoms to be present in the total of all the

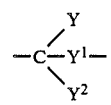

groups present.

In the compounds of the formula II,

is preferably $CF_3$ or —$CF_2Cl$; particularly preferentially

is —$CF_3$ and $R^1$ and $R^2$ are H, F or Cl.

The following are examples of compounds of the formula II:

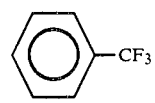 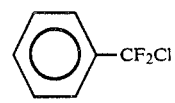

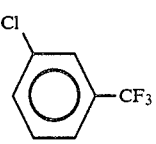 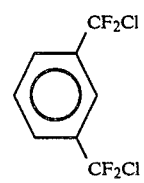

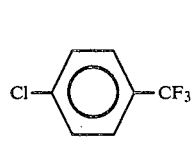 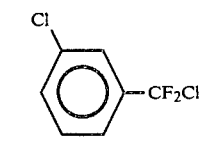

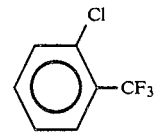 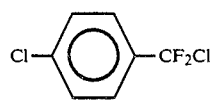

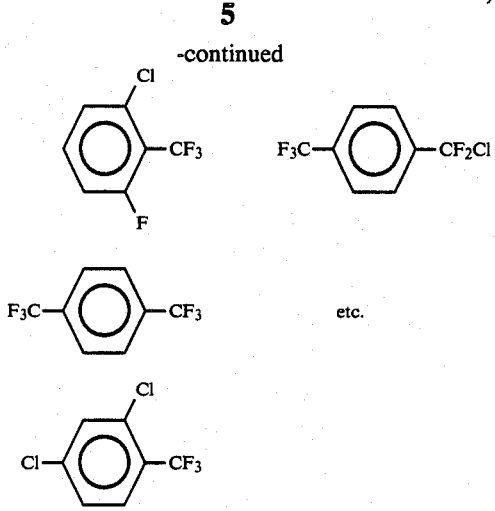

The individual compound particularly preferred is benzotrifluoride.

If mixtures of trihalogenomethyl aromatic compounds are employed, it is also possible, for example, to use concomitantly a fluorine-free trihalogenomethyl aromatic compound, such as, for example, benzotrichloride. Care must only be taken in all cases to ensure that a sufficient amount of a fluorine-containing trihalogenomethyl aromatic compound is then also present for F atoms to be present predominantly in the total of all the trihalogeno groups present.

Benzotrifluoride and the other trihalogenomethyl aromatic compounds mentioned above are known products which, in some cases, are also commercially available.

The fluorinating reagents or trihalogenomethyl aromatic compounds containing, as a predominent total or exclusively, fluorine atoms in the trihalogenomethyl groups are used in an amount which is at least approximately equivalent to the halogenated aliphatic carboxylic acids, preferably in an excess of about 5% to about 50%. A higher excess is only necessary in a given case if the halogenated aliphatic carboxylic acid employed contains an excessively high proportion of water. An "equivalent amount" means one trihalogenomethyl group in the trihalogenomethyl aromatic compounds per carboxyl group of the halogenated aliphatic carboxylic acids. The amount of benzotrifluoride equivalent to, for example, one mole of ω-H-perfluoropropionic acid is one mole, in accordance with the equation:

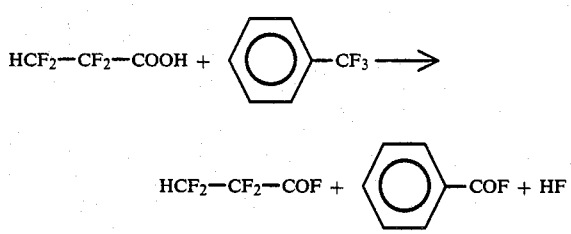

Catalysts suitable for the process according to the invention are, quite generally, Lewis acids. The oxides and/or halides and/or alcoholates of the following elements are preferred: Cu, Zn, Hg, B, Al, Sn, Ti, Zr, As, Sb, V, Fe and Ni. Amongst the halides, the chlorides and fluorides are, in turn, preferred; preferred alcoholates are the lower esters (in particular methyl and ethyl esters) of boric acid. The catalysts can be used either on their own or as mixtures with one another. Mixtures of the oxides and the chloride or fluoride of the same element in each case are preferred. The esters of boric acid are preferably used on their own. The amount of catalyst is, in general, between about 0.05 and about 25 mol %, preferably between 0.2 and about 5 mol %, relative to the halogenated aliphatic carboxylic acid used as starting material.

The reaction temperature is normally between about 20° and about 250° C., preferably between about 40° and about 200° C. and especially between about 60° and about 160° C.

In principle, the reaction can be carried out under normal, reduced or excess pressure. Reaction under normal or excess pressure is preferred. If the reaction is carried out under normal pressure, it is advantageous to separate off continuously the low-boilers formed, in order to be able to maintain the desired reaction temperature.

It is advantageous to stir the mixture thoroughly during the whole reaction period and thus to ensure uniform mixing. In general, the reaction time is between about 2 and about 60 hours, expecially between about 3 and about 30 hours.

In accordance with one exemplary procedure for carrying out the process according to the invention, the halogenated aliphatic carboxylic acid, the trihalogenomethyl aromatic compound(s) and the catalyst are combined and are heated (a) in the normal pressure variant in a vessel made of suitable material (for example polytetrafluoroethylene, metal or, in less usual cases, glass, etc.) until evolution of gas takes place. In the course of this, low-boiling products are discharged into a cooled receiver, together with the hydrogen halide formed at the same time, while higher-boiling products substantially remain in the reaction vessel.

(b) In the excess pressure variant, the starting materials are advantageously heated in an autoclave under autogenous pressure at the reaction temperature until the pressure remains constant for several hours. Low-boiling products, together with the hydrogen halide formed, are discharged from the autoclave as gas into a cooled metal vessel and are worked up. Higher-boiling products are distilled off direct from the reaction mixture, after adding a binder for HF.

If the halogenated aliphatic carboxylic acid fluoride formed cannot be separated by distillation from hydrofluoric acid formed at the same time, the mixture is preferably separated by one of the two methods following:

(a) Absorption of HF on NaF:

Excess NaF is added to the crude reaction mixture, which is stirred and then distilled. In the course of this, HF is bound in the form of $NaHF_2$. This can be carried out in the presence or absence of inert solvents, such as, for example, ethers, nitriles, sulfones etc.

(b) Removal of HF by means of trialkylamines:

The calculated amount of trialkylamine (about ⅓ mole of trialkylamine per mole of HF), for example triethylamine, is added to the crude reaction mixture, and the latter is distilled. The resulting adduct, trialkylamine.approx. 3HF, remains behind as a high-boiler. The adduct can be obtained in the pure form as a high-grade fluorinating agent by distillation.

The examples which follow are intended to illustrate the process according to the invention in greater detail.

The examples (of the invention) are followed by 2 further comparison examples, which show that ω-H-perfluoro-propionic acid does not react with benzotrifluoride even when heated for several hours at temperatures of up to about 190° C. in the absence of catalysts (Comparison Example 1) and that, similarly, no reaction takes place either between (non-halogenated) propionic acid and benzotrifluoride in the presence of $TiO_2$ and $TiCl^1$ as catalyst when heated for several hours at 130° C. (Comparison Example 2).

All of the compounds employed in the examples (of the invention and comparison) were of a technical grade of purity. The water content of the carboxylic acids was generally below one percent by weight.

(A) Examples of the invention

Only one example of the procedure under normal pressure (Example 1a) and one example of the procedure under excess pressure (Example 5a) are described here in detail. All the remaining examples were carried out analogously; the details which are still essential for these can be seen from the Table below.

EXAMPLE 1

(a) 78 g (0.53 mol) of $H-CF_2-CF_2-COOH$, 118 g (0. mol) of

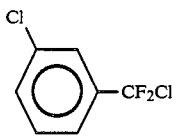

and 0.5 g (3.7 mmol) of $ZnCl_2$ (anhydrous) were initially placed in a glass flask equipped with a magnetic stirrer, a thermometer, a reflux condenser and a cold trap. The mixture was heated. Evolution of gas started above 60° C., and became vigorous at 120°–130° C. The mixture was heated until the bottom temperature reached 180° C. The cold trap (−78° C.) then held 65 g of colorless liquid, which was subjected to a refrigerated distillation. 40 g (51%) of $H-CF_2-CF_2-COF$ were obtained at b.p. 6°–9° C.

EXAMPLE 5

(a) The reaction was carried out in a 5-liter steel autoclave equipped with a reciprocating stirrer. A mixture of 1,500 g (10.27 mol) of $H-CF_2-CF_2-COOH$, 1,752 g (12 mol) of

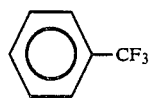

5 g (62.5 mmol) of $TiO_2$ and 5 g (26.3 mmol) of $TiCl_4$ was put into the autoclave and was heated to 130° C. under autogenous pressure. A pressure of 21 bar was reached after a reaction time of only 7 hours, and this pressure only increased to 22.5 bar after a further 14 hours at 130° C. The autoclave was cooled to 90° C. and depressurized via a cold trap made of stainless steel and holding 546 g (13 mol) of NaF and 500 ml of diglyme. Distillation of the contents of the trap gave 1,393 g (92%) of $H-CF_2-CF_2-COF$.

TABLE

Examples of the invention

| Example No. | Reaction vessel | X—R—COOH X—R— (mol) | Trihalogenomethyl aromatic compound(s) (mol) | Catalyst | (mmol) | Reaction temperature and time | Pressure | Yield of X—R—COF, % |
|---|---|---|---|---|---|---|---|---|
| 1a | Glass flask | $H-CF_2-CF_2$ (0.53) | Cl—C$_6$H$_4$—CF$_2$Cl (0.6) | $ZnCl_2$ | (3.7) | 120–130° C. | Atmospheric pressure | 51% |
| 1b | Glass flask | $H-CF_2-CF_2$ (0.5) | Cl—C$_6$H$_4$—CF$_2$Cl (0.6) | $TiO_2$ $TiCl_4$ | (6.25) (2.6) | 75° C.[1] | Atmospheric pressure | 57%[2,3] |
| 2 | Polytetrafluoroethylene flask | $H-CF_2-CF_2$ (0.5) | C$_6$H$_5$—CF$_3$ (0.5) | $TiO_2$ $TiCl_4$ | (25) (7.9) | | Atmospheric pressure | 68%[4] |
| 3 | Apparatus made of stainless steel | $H-CF_2-CF_2$ (2) | C$_6$H$_5$—CF$_3$ (2) | $TiO_2$ $TiCl_4$ | (25) (7.9) | 90–120° C. | Atmospheric pressure | 69%[4] |
| 4 | as in Example 3 | $H-CF_2-CF_2$ (2) | C$_6$H$_5$—CF$_3$ (2.2) | $TiO_2$ $SbF_3$ | (25) (11.2) | 100–125° C. 4 h | Atmospheric pressure | 44%[5] |
| 5a | Steel autoclave with stirrer | $H-CF_2-CF_2$ (10.27) | C$_6$H$_5$—CF$_3$ (12) | $TiO_2$ $TiCl_4$ | (62.5) (26.3) | 130° C. 21 h | 22.5 bar | 92% |

TABLE-continued

Examples of the invention

| Example No. | Reaction vessel | X—R—COOH X—R— (mol) | Trihalogenomethyl aromatic compound(s) (mol) | Catalyst | (mmol) | Reaction temperature and time | Pressure | Yield of X—R—COF, % |
|---|---|---|---|---|---|---|---|---|
| 5b | Steel autoclave with stirrer | H—CF$_2$—CF$_2$ (15) | Ph—CF$_3$ (17.55) | TiO$_2$ TiCl$_4$ | (62.5) (26.3) | 130° C. 16 h | 21 bar | 93% |
| 5c | Steel autoclave with stirrer | H—CF$_2$—CF$_2$ (15) | Ph—CF$_3$ (17.55), Ph—CCl$_3$ (0.1) | TiO$_2$ TiCl$_4$ | (62.5) (26.5) | 130° C. 19 h | 20 bar[6] | 94%[7] |
| 5d | Steel autoclave with stirrer | H—CF$_2$—CF$_2$ (15) | Ph—CF$_3$ (17.55), Ph—CCl$_3$ (0.13) | TiO$_2$ TiCl$_4$ | (62.5) (26.3) | 130° C. 6 h | 20.5 bar | 90% |
| 6 | Steel autoclave with stirrer | H—CF$_2$—CF$_2$ (2) | Ph—CF$_3$ (2.2) | TiO$_2$ | (12.5) | 130° C. 19 h | 18 bar | 76%[5] |
| 7a | as in Example 5a | H—CF$_2$—CF$_2$ (2) | Ph—CF$_3$ (2.2) | Al$_2$O$_3$ | (49) | 130° C. 66 h | 26 bar | 24%[5] |
| 7b | as in Example 5a | H—CF$_2$—CF$_2$ (2) | Ph—CF$_3$ (2.2), Ph—CCl$_3$ (0.050) | Al$_2$O$_3$ AlCl$_3$ | (9.8) (7.5) | 130° C. 45 h | 17 bar | 63% |
| 8 | as in Example 5a | H—CF$_2$—CF$_2$ (0.25) | 1,4-(CF$_2$Cl)$_2$C$_6$H$_4$ (0.15) | TiO$_2$ TiCl$_4$ | (12.5) (5.3) | ~100° C. | Atmospheric pressure | 74%[3] |
| 9 | as in Example 5a | H—CF$_2$—CF$_2$ (2) | Ph—CF$_3$ (1.47), Ph—CCl$_3$ (0.750) | TiO$_2$ TiCl$_4$ | (12.5) (5.3) | 90° C., 2 h and 130° C., 18 h | (16 bar) 35 bar[8] | 75%[4] |
| 10a | as in Example 5a | H—CF$_2$—CF$_2$ (2) | Cl—C$_6$H$_4$—CF$_3$ (2.2) | TiO$_2$ TiCl$_4$ | (12.5) (5.3) | 130° C. 18 h | 20 bar[9] | 77% |
| 10b | as in Example 5a | H—CF$_2$—CF$_2$ (2) | Cl—C$_6$H$_4$—CF$_3$ (2.2) | TiCl$_4$ TiF$_4$ | (5.3) (8.1) | 130° C. 20 h | 13 bar | 35% |
| 10c | as in Example 5a | H—CF$_2$—CF$_2$ (2) | Cl—C$_6$H$_4$—CF$_3$ (2.2) | TiO$_2$ TiF$_4$ | (12.5) (8.1) | 130° C. 20 h | 20 bar[10] | 77% |
| 11 | as in Example 5a | H—CF$_2$—CF$_2$ (2) | 2-Cl-C$_6$H$_4$—CF$_3$ (2.2) | TiO$_2$ TiCl$_4$ | (12.5) (5.3) | 130° C. 18 h | 20 bar | 77% |

TABLE-continued

Examples of the invention

| Example No. | Reaction vessel | X—R—COOH X—R— (mol) | Trihalogenomethyl aromatic compound(s) (mol) | Catalyst | (mmol) | Reaction temperature and time | Pressure | Yield of X—R—COF, % |
|---|---|---|---|---|---|---|---|---|
| 12 | as in Example 5a | H—CF$_2$—CF$_2$ (2) | 2-Cl, 3-F-C$_6$H$_3$—CF$_3$ (2.2) | TiO$_2$ TiCl$_4$ | (12.5) (5.3) | 130° C. 19 h | 14 bar | 43% |
| 13 | as in Example 5a | H—CF$_2$—CF$_2$ (2) | C$_6$H$_5$—CF$_3$ (2.2) / C$_6$H$_5$—CCl$_3$ (0.050) | ZnO ZnCl$_2$ | (12.3) (7.4) | 130° C. 45 h | 15 bar | 57% |
| 14 | as in Example 5a | H—CF$_2$—CF$_2$ (2) | C$_6$H$_5$—CF$_3$ (2.2) / C$_6$H$_5$—CCl$_3$ (0.050) | SbCl$_5$ | (6.7) | 130° C. 39 h | 18 bar | 67% |
| 15 | as in Example 5a | H—CF$_2$—CF$_2$ (2) | C$_6$H$_5$—CF$_3$ (2.2) / C$_6$H$_5$—CCl$_3$ (0.010) | TiO$_2$ SnCl$_4$ | (12.5) (3.8) | 130° C. 19 h | 16 bar | 70% |
| 16 | as in Example 5a | H—CF$_2$—CF$_2$ (1) | C$_6$H$_5$—CF$_3$ (1.1) / C$_6$H$_5$—CCl$_3$ (0.026) | Fe$_2$O$_3$ FeCl$_3$ | (6.3) (6.2) | 130° C. 15 h | 13 bar | 31% |
| 17 | as in Example 5a | H—CF$_2$—CF$_2$ (2) | C$_6$H$_5$—CF$_3$ (2.2) / C$_6$H$_5$—CCl$_3$ (0.026) | HgO HgCl$_2$ | (4.6) (3.7) | 130° C. 18 h | 14 bar | 44% |
| 18 | as in Example 5a | H—CF$_2$—CF$_2$ (1) | C$_6$H$_5$—CF$_3$ (1.1) / C$_6$H$_5$—CCl$_3$ (0.013) | TiO$_2$ NiCl$_2$ | (12.5) (7.7) | 130° C. 19 h | 18 bar | 64% |
| 19 | as in Example 5a | H—CF$_2$—CF$_2$ (2) | C$_6$H$_5$—CF$_3$ (2.2) / C$_6$H$_5$—CCl$_3$ (0.026) | CuO CuCl$_2$.2H$_2$O | (12.6) (5.9) | 130° C. 15 h | 14 bar | 43% |
| 20 | as in Example 5a | H—CF$_2$—CF$_2$ (15) | C$_6$H$_5$—CF$_3$ (17.55) | B$_2$O$_3$ | (72) | 130° C. 19 h | 24 bar | 89% |
| 20a | as in Example 5a | H—CF$_2$—CF$_2$ (15) | C$_6$H$_5$—CF$_3$ (18) | B(OCH$_3$)$_3$ | (96) | 130° C. 19 h | 20.5 bar | 84% |
| 21 | as in Example 5a | CF$_3$ (5) | C$_6$H$_5$—CF$_3$ (5.4) | TiO$_2$ TiCl$_4$ | (25) (10.5) | 130° C. 20 h | 44 bar[11] | 90%[5] |
| 22 | as in Example 5a | CF$_3$—(CF$_2$)$_6$ (0.7) | C$_6$H$_5$—CF$_3$ (0.7) | TiO$_2$ TiCl$_4$ | (12.5) (5.3) | 130° C. 20 h | 6 bar | 60%[12] |
| 23 | Glass flask | CF$_3$—(CF$_2$)$_6$ (0.35) | Cl-C$_6$H$_4$—CF$_2$Cl (0.45) | TiO$_2$ TiCl$_4$ | (6.25) (2.6) | 120–130° C. | Atmospheric pressure | 85%[12] |

TABLE-continued

Examples of the invention

| Example No. | Reaction vessel | X—R—COOH  X—R— (mol) | Trihalogenomethyl aromatic compound(s) (mol) | Catalyst | (mmol) | Reaction temperature and time | Pressure | Yield of X—R—COF, % |
|---|---|---|---|---|---|---|---|---|
| 24 | as in Example 5a | CHFCl (2) | —CF$_3$ (2.2) | TiO$_2$ TiCl$_4$ | (12.5) (5.3) | 130° C. 18 h | 18 bar | 47%[13] |
| 25 | Glass flask | CCl$_3$ (0.4) | 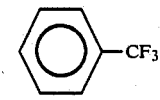 with CF$_2$Cl and CF$_2$Cl (0.22) | TiO$_2$ TiCl$_4$ | (12.5) (5.3) | 50–90° C. | Atmospheric pressure | 70%[12] |
| 26 | as in Example 5a | HOOC—CF$_2$—CF$_2$[14] (~0.8) | 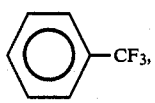—CF$_3$ (2) and 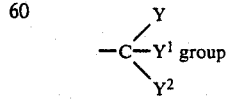—CCl$_3$ (0.050) | TiO$_2$ TiCl$_4$ | (12.5) (5.3) | 130° C. 20 h | 12 bar | 20% |

Unless otherwise specified, the acid fluoride was worked up with the addition of $(C_4H_9)_3N$.
[1] Gas evolution from 45° C.
[2] A further 10% of H—CF$_2$—CF$_2$—COCl were isolated
[3] Purification by distillation without adding $(C_4H_9)_3N$
[4] Purification by distillation with the addition of NaF/CH$_3$CN
[5] Purification by distillation with the addition of NaF
[6] Reached after only 3 hours
[7] Purification by distillation with the addition of $(C_3H_7)_3N$
[8] Reached after a total of only 5 hours
[9] After 5 hours: 17 bar
[10] Reached after 8 hours
[11] After 6 hours: 40 bar
[12] NaF was added to the reaction mixture and the latter was distilled

[13] Distillation after  $(H)_2NC_2H_5$ had been pumped into the autoclave

[14] Contained an unknown amount of water (B) Comparison examples

COMPARISON EXAMPLE 1

73 g (0.5 mol) of H—CF$_2$—CF$_2$—COOH and 102 g (0.7 mol) of

—CF$_3$ were initially placed in a 250 ml stainless steel autoclave. Heating was carried out for 16 hours at 140° C., 23 hours at 170° C. and 5 hours at 190° C.

When the autoclave had cooled to room temperature, it was no longer under pressure. No HF and no H—CF$_2$—CF$_2$—COF could be detected in the reaction mixture.

COMPARISON EXAMPLE 2

148 g (2 mol) of CH$_3$—CH$_2$—COOH, 321 g (2.2 mol) of

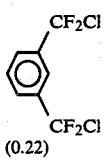—CF$_3$, 1 g (12.5 mmol) of TiO$_2$ and 1 g (5.3 mmol) of TiCl$_4$ were heated at 130° C. for 16 hours in a 1-liter iron autoclave equipped with a reciprocating stirrer. A pressure of 2 bar was set up. Working up gave no indication of the formation of CH$_3$—CH$_2$—COF.

We claim:

1. A process for the preparation of a halogenated aliphatic carboxylic acid fluoride, which comprises reacting in the presence of a Lewis acid as catalyst a halogenated aliphatic carboxylic acid with a trihalogenomethyl aromatic fluorinating reagent containing, as a predominant total or exclusively, fluorine atoms in the trihalogenomethyl groups.

2. The process as claimed in claim 1, wherein the halogenated aliphatic carboxylic acid is a compound of the formula I $$X—R—COOH \quad (I)$$

where R is a divalent aliphatic $C_1$–$C_{10}$ radical in which at least half of the H atoms have been replaced by halogen and X is H, halogen or COOH.

3. The process as claimed in claim 2, wherein the halogen is selected from the group consisting of F and Cl.

4. The process as claimed in claim 3, wherein the

group in the fluorinating reagent of the formula II is —CF$_3$ or —CF$_2$Cl.

5. The process as claimed in claim 3, wherein the

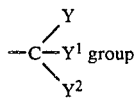 group in the fluorinating agent of the formula II is —CF₃ and R¹ and R², independently of one another, are H, F or Cl.

6. The process as claimed in claim 1, wherein the fluorinating reagent is used in an amount which is at least approximately equivalent to the halogenated aliphatic carboxylic acid.

7. The process as claimed in claim 1, wherein the fluorinating reagent is a trihalogenomethyl aromatic compound of the formula II

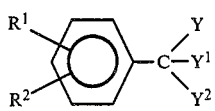 (II)

or mixtures thereof, where Y, Y¹ and Y², independently of one another, are selected from the group consisting of F and Cl, and R¹ and R², independently of one another, are selected from the group consisting of H, halogen or

and at least twice as many F atoms as Cl atoms are present in the total of all the

groups present.

8. The process as claimed in claim 7, wherein in the definition of R¹ and R², the halogen is selected from the group consisting of F and Cl.

9. The process as claimed in claim 1, wherein the Lewis acid catalyst is selected from the group consisting of an oxide, a halide, an alcoholate and mixtures thereof of the elements Cu, Zn, Hg, B, Al, Sn, Ti, Zr, As, Sb, V, Fe, and Ni.

10. The process as claimed in claim 1, wherein the catalyst is employed in an amount between about 0.05 and about 25 mol% relative to the halogenated aliphatic carboxylic acid.

11. The process as claimed in claim 1, wherein the catalyst is employed in an amount between about 0.2 and about 5 mol% relative to the halogenated aliphatic carboxylic acid.

12. The process as claimed in claim 1, wherein the reaction is carried out at a temperature between about 20° and about 250° C.

13. The process as claimed in claim 1, wherein the reaction is carried out at a temperature between about 40° and about 200° C.

14. The process as claimed in claim 1, wherein the reaction is carried out at a temperature between about 60° and about 160° C.

* * * * *